United States Patent [19]

Kawaguchi

[11] Patent Number: 4,827,746

[45] Date of Patent: May 9, 1989

[54] SAMPLING METHOD FOR OSCILLATORY DENSIMETER

[75] Inventor: Kenji Kawaguchi, Kyoto, Japan

[73] Assignee: Kyoto Electronics Manufacturing Co., Ltd., Kyoto, Japan

[21] Appl. No.: 143,251

[22] Filed: Dec. 29, 1987

[30] Foreign Application Priority Data

Dec. 29, 1986 [JP] Japan ................................. 61-312913

[51] Int. Cl.[4] ............................................. G01N 9/00
[52] U.S. Cl. .................................... 73/32 A; 73/863.01
[58] Field of Search ..................... 73/32 A, 32 R, 863, 73/863.01, 863.83

[56] References Cited

U.S. PATENT DOCUMENTS 4,074,562  2/1978  North ................................. 73/32 A Primary Examiner—John Chapman
Attorney, Agent, or Firm—Lowe, Price, LeBlanc, Becker & Shur

[57] ABSTRACT

An oscillation period of an oscillating tube of an oscillatory densimeter is detected while liquids of which densities are to be measured are introduced into the oscillating tube. When the oscillation period exceeds a predetermined threshold, a time for which the introduction of liquids should be further continued is determined by multiplying the time from the start of the introduction to occurrence of the exceeding by a predetermined ratio.

5 Claims, 3 Drawing Sheets

SAMPLING START

CHANGE OF
OSCILLATION PERIOD

SAMPLING END

SAMPLING METHOD FOR OSCILLATORY DENSIMETER

BACKGROUND OF THE INVENTION

This invention relates to an oscillatory densimeter and, in particular, to a method of sampling into the oscillatory densimeter liquids of which densities are to be measured.

The oscillatory densimeter is an instrument to measure densities of liquids on the basis of oscillation periods of an oscillating tube filled with the liquids. The oscillating tube is a thin tube shaped like a letter U, as illustrated in FIG. 1. A detailed description with reference to FIG. 1 will be given later.

The liquids are introduced into the oscillating tube by applying pressure to the liquids or by lowering the pressure in the tube. The introduction is usually stopped a predetermined time $T_0$ after start of the introduction, without respect to the viscosities of the liquids. When several liquids are sampled successively and automatically, the time $T_0$ is selected to be long enough for the oscillating tube to be filled with a liquid of which viscosity is the highest of all. As a result, the lower the viscosity of another liquid is, the larger is the quantity of that liquid which is introduced into the tube for time $T_0$ that must be prepared for the sampling.

SUMMARY OF THE INVENTION

An object of the present invention is to provide a method of sampling the liquids for the oscillatory densimeter, which compensates for the difference between the viscosities of the liquids and requires for the sampling only a quantity of each liquid necessary to fill the oscillation tube. Loss of the liquids at the sampling can thus be made as small as possible by the method. Additionally, erroneous measurement before the oscillating tube is completely filled with the liquids can be avoided.

To achieve the object, the oscillation period of the oscillating tube continues to be detected while the liquids are introduced into the tube. A sudden change takes place in the oscillation period when the liquid reaches a point of the tube. The timing to stop the introduction is determined depending on a period of time needed for the change to take place. The introduction is stopped another period of time after the change is detected so that the U-shaped thin tube can be completely filled with the liquid. The latter time is determined by multiplying the former time by a predetermined ratio.

The time needed to measure the oscillation to detect the change during the introduction should be a shorter time than that need to measure the oscillation to calculate the densities after the introduction is completed because, when the liquids have comparatively small viscosities, a considerable quantity of excessive liquids might have been supplied into the tube after the change of oscillation period actually occurs but before the change is detected.

BRIEF DESCRIPTION OF THE DRAWING

An embodiment of the invention will now be described by way of example and with reference to the accompanying drawings, in which.

DETAILED DESCRIPTION OF THE PREFERRED EMBODIMENT OF THE INVENTION

Figure 1:
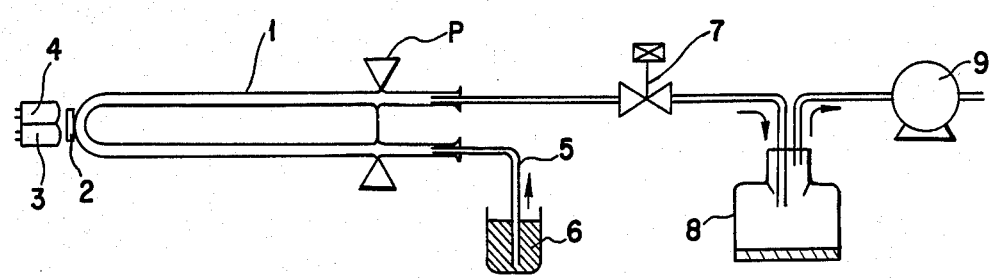
FIG. 1 is a schematic diagram of the oscillatory densimeter to which the method of the present invention is to be applied.

With reference to FIG. 1, a U-shaped thin oscillating tube 1 is supported by a supporter P. A magnet 2 is attached to tube 1 at the bottom of the U-shape, and oscillates together with the tube. A detection signal, which is an electric signal indicative of the oscillation of magnet 2, is generated by a detection head 3. The density of the liquid which fills tube 1 is calculated on the basis of the detection signal by a circuit as described later with reference to FIG. 2. The detection signal is also utilized to drive oscillating tube 1 by driving head 4. An end of tube 1 is open via a sampling tube 5 in a vessel 6 in which the liquid is supplied. The liquid is introduced into tube 1 by a pump 9, which is connected to the other end of tube 1 through a valve 7 and another vessel 8. The liquid may otherwise be introduced by applying pressure to the liquid in vessel 6 by a compressor (not shown) of known kind.

Figure 2:
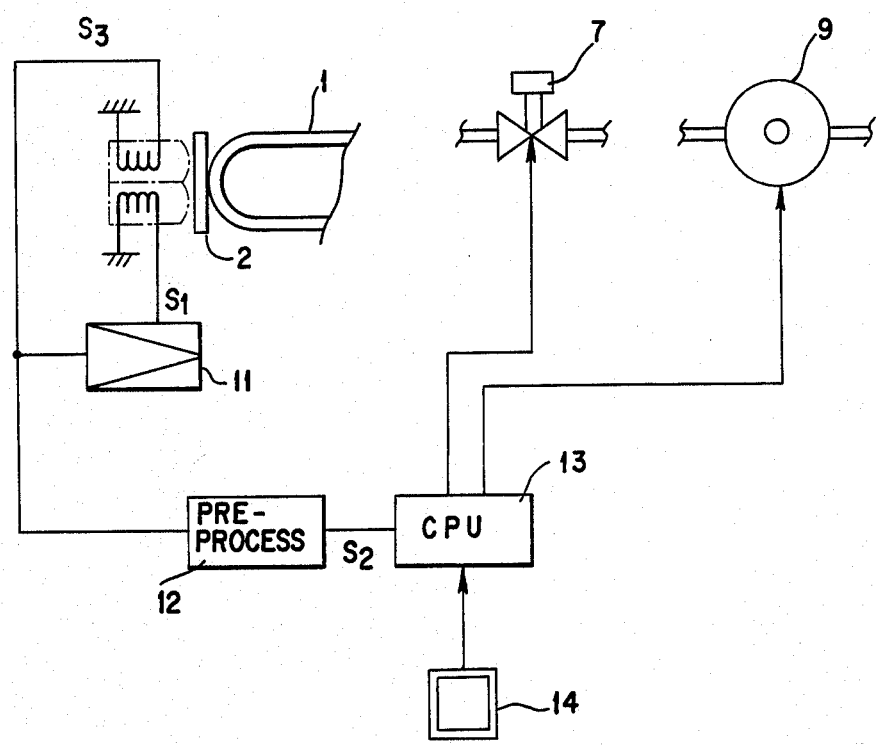
FIG. 2 is a block diagram of a circuit to achieve the present invention.

With reference to FIG. 2, detection signal $S_1$ generated by detection head 3 is applied to a pre-processing circuit 12 after being amplified by an amplifier 11.

A number signal $S_2$, which indicates the number of reference clock pulses counted for a predetermined number of periods of detection signal $S_1$, is generated by pre-processing circuit 12 and applied to a CPU 13, which determines the period of detection signal $S_1$ on the basis of number signal $S_2$ and calculates the density of the liquid. The output of amplifier 11 is, as it is or after being converted to a rectangular pulse signal, applied to driving head 4. The circuit, as far as described above, has an identical structure to that of the prior art.

Figure 3:
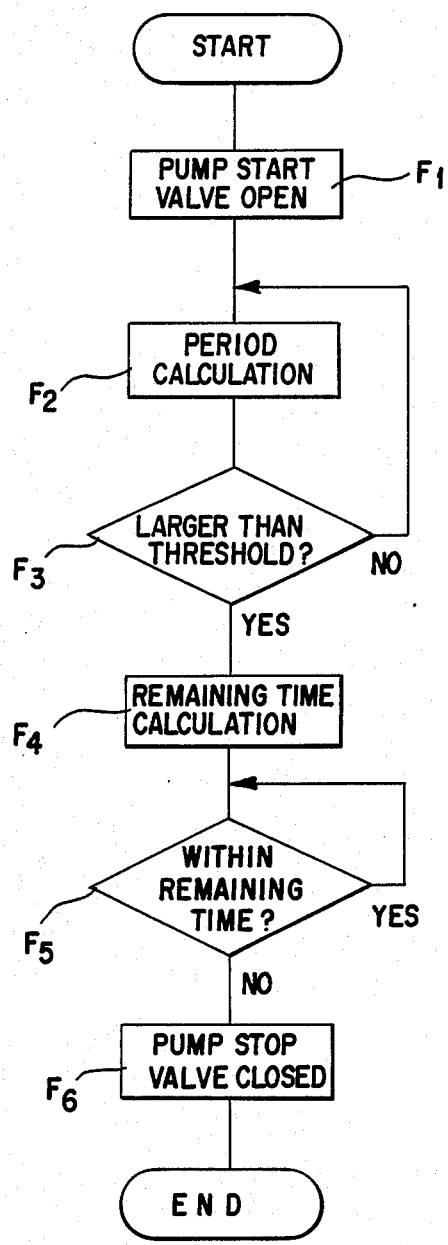
FIG. 3 is a flow chart illustrating operation of a CPU 13 with the invention.

With reference to FIG. 3, CPU 13 starts the automatic sampling program of the present invention when a start key prepared on a keyboard (which is not illustrated in the drawings) is turned on. Valve 7 is opened and motor 9 starts being driven at step $F_1$. Simultaneously, detection of the oscillation by detection head 3 and driving of oscillating tube 1 by driving head 4 are started. The period of detection signal $S_1$ is calculated on the basis of number signal $S_2$ at step $F_2$.

The oscillation period of oscillating tube 1 containing gases is clearly distinctive from that of the tube containing liquids. The former is considerably smaller than the latter. Accordingly, a threshold value is prepared in a memory means CPU 13 to determine whether the contents of oscillating tube 1 are gases or liquids. The calculated period is compared with the threshold value at step $F_3$. The calculation and comparison are repeated as long as the calculated period is smaller than the threshold. After the calculated period exceeds the threshold, a remaining time $t_2$ is calculated at step $F_4$. The calculation process will be described later in detail. At step $F_5$ it is determined whether remaining time $t_2$ has passed after the change of the oscillation period is detected. After the time is determined to have passed, pump 9 is stopped and valve 7 is closed simultaneously at step $F_6$.

Figure 4A:
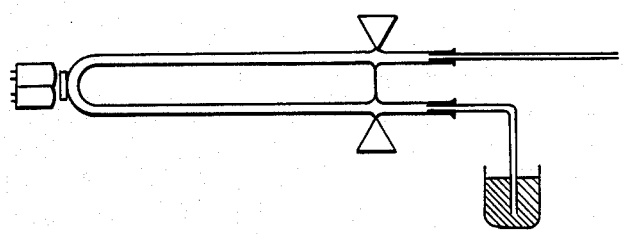
FIGS. 4(*a*), 4(*b*) and 4(*c*) are schematic views respectively illustrating conditions of the liquid to be sampled when the sampling starts, when the liquid reaches a point (a) and when the sampling finishes.
Figure 4B:
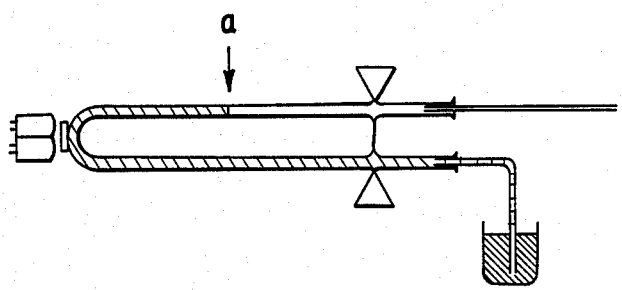
Figure 4C:
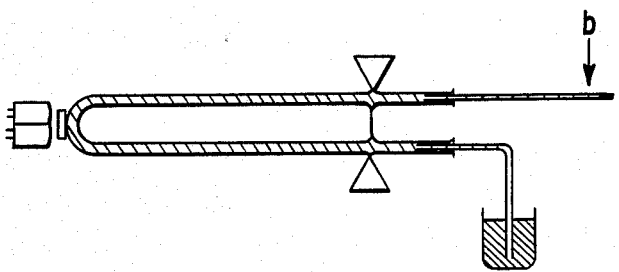

Remaining time $t_2$ is determined on the basis of an empirical fact as follows. It is experimentally confirmed that the change of oscillation period takes place when the liquid to be sampled reaches approximately point a as indicated in FIG. 4(b). As seen from Table 1 infra, when time $t_0$ and time $t_1$ are needed from the sampling start for the liquid to reach point a and another point b as indicated in FIG. 4(c) respectively, a ratio of $t_1$ to $t_0$ is approximately constant without respect to the kinematic viscosity of the liquid. This is understandable as, the quantity of the liquid which passes a cross section of tube 1 per unit of time is supposed to be constant throughout the introduction. Accordingly, the remaining time $t_2 = t_1 - t_0$ is obtained by an equation $$t_2 = t_0 \times r$$

wherein $r = (t_1/t_0) - 1$.

Number signal $S_2$ to calculate the densities of the liquids is obtained corresponding usually to hundreds of periods of detection signal $S_1$. As the calculation at step $F_2$ is, on the other hand, only to detect the change of the oscillation period and not to determine the densities, number signal $S_2$ corresponding only to several periods of detection signal $S_1$ is effective enough. As a result, the time needed for measurement of the oscillation period during the introduction can be much shorter than the time needed for the density calculation, which enables detection of a precise timing of the change of the oscillation period.

According to the present invention, the change of the oscillation period of the oscillation thin tube is detected so that the timing to stop the introduction of liquids into the tube can be determined on the basis of the time needed for the change to occur. As a result, a most suitable constant quantity of the liquids can be introduced into the tube regardless of the viscosities of the liquids.

TABLE 1

| kinematic viscosity (cst) | $t_0$ (sec) | $t_1$ (sec) | $t_1/t_0$ |
| --- | --- | --- | --- |
| 1.0 | 1.1 | 2.0 | 1.82 |
| 1.7 | 1.8 | 3.4 | 1.89 |
| 2.8 | 2.9 | 5.4 | 1.86 |
| 7.4 | 7.6 | 15.0 | 1.97 |
| 11.0 | 10.5 | 20.2 | 1.92 |
| 16.0 | 17.5 | 34.6 | 1.98 |
| 25.0 | 28.5 | 54.3 | 1.91 |
| 42.0 | 52.8 | 100.0 | 1.89 |
| 73.0 | 84.6 | 159.8 | 1.89 |

What we claim is:

1. A method of sampling a liquid, the density of which is to be measured, into an oscillating tube of an oscillatory densimeter, comprising the steps of:
   staring introduction of the liquid into the densimeter tube and simultaneously starting oscillating of the tube while continually detecting an oscillating period thereof;
   determining a first time period that elapses after said starting to when the oscillation period exceeds a predetermined threshold value; and
   stopping the introduction of more of the liquid into the oscillating tube a selected second period of time after said first time period, said second time period being dependent on said first time period.

2. A method of sampling as recited in claim 1, wherein:
   said second period of time is determined by multiplying the first time period by a number which is empirically determined.

3. A method of sampling as recited in claim 1, further comprising the step of:
   after said second time period determining an oscillation period of the tube to determine a density of the liquid, wherein each measurement of the oscillation period during the introduction step is performed within a shorter time than the time needed for measurement of the oscillation period to determine the density of the liquid.

4. A method for efficiently and economically determining the densities of a plurality of liquids, by sampling individual liquids into an oscillating tube of an oscillatory densimeter, comprising the steps of:
   starting introduction of a selected first one of said plurality of liquids into the densimeter tube and simultaneously starting oscillating of the tube while continually detecting an oscillation period thereof;
   determining for said first liquid a first time period that elapses after said starting to when the oscillation period exceeds a predetermined threshold value;
   stopping the introduction of more of the first liquid into the oscillating the when the first liquid has filled the tube a second period of time after said first time period; determining the ratio of said second period of time divided by said first time period for said first liquid;
   selecting another liquid of said plurality of liquids and repeating said steps of starting introduction and determining a corresponding first time period for said another liquid;
   determining for said another liquid a corresponding second period of time equal to said corresponding first time period therefor multiplied by said ratio;
   stopping the introduction of more of said another liquid into the oscillating tube said corresponding second period of time after said corresponding first time period therefor; and
   repeating the steps of the preceding three paragraphs of this claim for each remaining liquid in said plurality of liquids the densities of which are to be determined.

5. A method according to claim 4, further comprising the step of:
   for each one of said plurality of liquids sampled, after said second time period determining an oscillation period to determine a density of the liquid, wherein each measurement of the oscillation period of the tube during the introduction step is performed within a shorter time than the time needed for measurement of the oscillation period to determine the density of the liquid.

* * * * *